(12) United States Patent
Lobmaier et al.

(10) Patent No.: US 6,248,913 B1
(45) Date of Patent: Jun. 19, 2001

(54) CATALYSTS FOR OLEFIN SELECTIVE EPOXIDATION WITH ATMOSPHERIC OXYGEN

(75) Inventors: Gerhard Lobmaier, Gersthofen; Wolfgang Anton Herrmann, Freising; Rolf Peter Schulz, Dinslaken, all of (DE)

(73) Assignee: Aventis Research & Technologies GmbH & Co. KG (DE)

(*) Notice: Subject to any disclaimer, the term of this patent is extended or adjusted under 35 U.S.C. 154(b) by 0 days.

(21) Appl. No.: 09/462,451

(22) PCT Filed: Jul. 8, 1998

(86) PCT No.: PCT/EP98/04240

§ 371 Date: Jan. 7, 2000

§ 102(e) Date: Jan. 7, 2000

(87) PCT Pub. No.: WO99/02261

PCT Pub. Date: Jan. 21, 1999

(30) Foreign Application Priority Data

Jul. 11, 1997 (DE) .............................. 197 29 837
Jun. 24, 1998 (DE) .............................. 198 28 012

(51) Int. Cl.[7] .......................... C07F 11/00; B01J 31/00; C07D 327/00; C07D 307/00
(52) U.S. Cl. ........................ 556/57; 502/150; 502/162; 546/2; 549/3; 549/206
(58) Field of Search ................ 556/57; 546/2; 359/3, 206; 502/150, 162

(56) References Cited

U.S. PATENT DOCUMENTS

| 3,668,227 | 6/1972 | Mattucci et al. ............... 260/429 J |
| 3,956,180 | 5/1976 | Cavitt ........................... 252/431 R |

FOREIGN PATENT DOCUMENTS

| 2070406 | 9/1971 | (FR) . |
| 2115752 | 7/1972 | (FR) . |
| 96/20788 | 7/1996 | (WO) . |

*Primary Examiner*—Porfirio Nazario-Gonzalez
(74) *Attorney, Agent, or Firm*—Connolly Bove Lodge & Hutz LLP

(57) ABSTRACT

A catalyst for the selective oxidation of olefins in the presence of air or oxygen, comprising a compound of the formula (1)

$$Mo_xO_y(L)_z \qquad (1)$$

where
x is 1, 2 or 3,
y is an integer from 0 to 2x+1,
z is an integer from 1 to 2x,
wherein the ligand L is a compound of the formula (2) or (3)

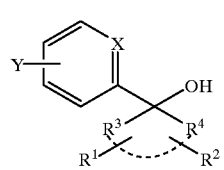

(2)

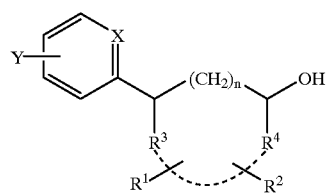

(3)

where
n is 0 or 1,
X is a nitrogen, oxygen or sulfur atom,
Y is hydrogen, $C_1$–$C_8$-alkyl, $C_1$–$C_8$-alkoxy, F, Cl, Br, I, $COOCH_3$, $C_6$–$C_{14}$-aryl or $C_3$–$C_8$-cycloalkyl,
$R^3$ and $R^4$ form a ring containing from 4 to 8 carbon atoms onto which one or two aromatic rings may be fused,
$R^1$ and $R^2$ are hydrogen, branched or straight-chain $C_1$–$C_{12}$-alkyl or branched or straight-chain $C_1$–$C_{12}$-haloalkyl which substitute the ring formed by $R^3$ and $R^4$ and/or the rings fused onto this ring,
or the ligand L is a compound of the formula (4) or (5)

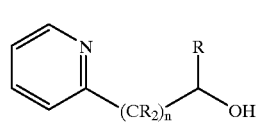

(4)

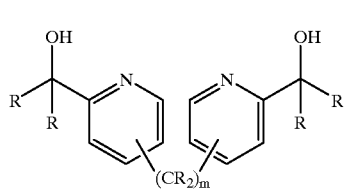

(5)

where R is hydrogen, $C_1$–$C_8$-alkyl, $C_1$–$C_8$-alkoxy, $COOCH_3$, carbonyl oxygen, $C_6$–$C_{14}$-aryl or $C_3$–$C_8$-cycloalkyl and n is 1 or 2 and m is from 1 to 6.

7 Claims, No Drawings

CATALYSTS FOR OLEFIN SELECTIVE EPOXIDATION WITH ATMOSPHERIC OXYGEN

The present invention relates to compounds which selectively catalyze the epoxidation of olefins by atmospheric oxygen, to a process for preparing them and to their use.

Epoxides (oxiranes), for example ethylene oxide, propylene oxide, 1,2-butene oxide and similar epoxides, are widely used intermediates in the production of many products. The oxirane function in such compounds is very reactive and ring-opening reactions take place in the presence of nucleophilic reactants. Thus, epoxides can, for example, be hydrolyzed to give glycols which are employed as deicing agents or as reactive monomers for preparing condensation polymers.

Polyether polyols prepared by ring-opening polymerization of epoxides are widely used as intermediates in the production of polyurethane foams, elastomers, coatings, sealing compositions or similar products.

The reaction of epoxides with alcohols leads to glycol ethers which are used, for example, as polar solvents.

For the preparation of epoxides, many different compounds which are supposed to selectively catalyze the epoxidation of alkenes have been developed.

Thus, for example, Huybrecht (J. Mol. Catal. 71, 129 (1992); EP-A-311983) describes the epoxidation of olefins using hydrogen peroxide in the presence of titanium silicate compounds as catalyst. However, the process disclosed here cannot be implemented economically, since hydrogen peroxide is firstly a relatively expensive oxidizing agent and secondly cannot be utilized completely since it partly decomposes into water and oxygen.

The epoxidation of propylene using atmospheric oxygen in the presence of tungsten- or molybdenum-containing catalysts is described in DE-C-22 35 229. The epoxidation reaction is carried out in a solvent which can be oxidized by oxygen to form hydroperoxides. However, the hydroperoxides formed undergo further reactions to give oxygen-containing by-products, generally alcohols, which are obtained as coproducts of the reaction.

Molybdenum complexes which catalyze the epoxidation of ethylene by t-butyl hydroperoxide (TBHP) have been described by Kelly et al. (Polyhedron, Vol. 5, 271–275, (1986)). As complexes having a high catalytic activity, mention is made of complexes such as $MoO_2(8\text{-hydroxyquinoline})_2$, $MoO_2(\text{phenylene-bissalicylimine})$ (=$MoO_2(\text{salphen})$), $MoO_2(5\text{-nitroso-8-hydroxyquinoline})_2$. The actual active catalyst is a molybdenum complex which has added-on TBHP and one equivalent of epoxide.

Although the process proceeds with high selectivity, an expensive oxidizing agent is used. In addition, reproducibility problems occur, which prevents industrial use of the process.

The epoxidation of 1-octene using molybdenum catalysts has been subject matter of a study in J. Prakt. Chem. (1992, 334, 165–175). In the presence of molybdenyl acetylacetonate, a selectivity for 1,2-epoxyoctane of 34% is found; in the presence of molybdenum trioxide, the selectivity is 28%. Likewise, it is confirmed that the position of the transition metal in the Periodic Table and its oxidation state have by far the greatest influence on the catalyst activity, with the structure of the catalyst complex itself playing only a subordinate role.

In studies of epoxidation catalysts (J. Prakt. Chem. 1984, 326, 1025–26; DD-A-159 075), the complex $MoCl_2(NO)_2$(HMP) (HMP=hexa-methylphosphoramide) containing divalent molybdenum displayed the best epoxide selectivity of 43.8%, but has the disadvantage of using the carcinogenic HMP ligand.

Epoxidation catalysts based on molybdenum which allow olefins to be oxidized selectively in the presence of atmospheric oxygen are disclosed in DE-A44 47 233 and DE-A-44 47 231, but these catalysts too do not display satisfactory epoxide selectivities, particularly not in the case of octene oxide.

Heterogenized Mo complexes for epoxidizing olefins are also known from WO-A-94/04268. However, the compounds disclosed have the disadvantage of needing expensive hydroperoxides and, moreover, the ligands used are not sufficiently oxidation-stable in the presence of oxygen.

It has surprisingly been found that a series of bidentate, cyclically substituted ligands give excellent yields and selectivities in the oxidation of olefins using atmospheric oxygen.

The invention accordingly provides catalysts for the selective oxidation of olefins in the presence of air or oxygen, comprising compounds of the formula (1)

$$Mo_xO_y(L)_z \qquad (1)$$

where x is 1, 2 or 3, y is an integer from 0 to 2x+1, preferably y is $\geq 1$, z is an integer from 1 to 2x and 2y+z is preferably 5 or 6, wherein the ligand L is a compound of the formula (2) or (3)

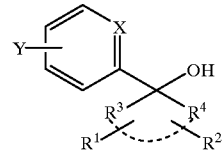

(2)

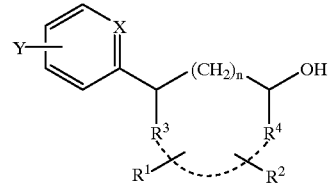

(3)

where n is 0 or 1,

X is a nitrogen, oxygen or sulfur atom,

Y is hydrogen, $C_1$–$C_8$-alkyl, $C_1$–$C_8$-alkoxy, F, Cl, Br, I, $COOCH_3$, $C_6$–$C_{14}$-aryl or $C_3$–$C_8$-cycloalkyl, $R^3$ and $R^4$ form a ring containing from 4 to 8 carbon atoms onto which one or two aromatic rings may be fused, $R^1$ and $R^2$ are hydrogen, branched or straight-chain $C_1$–$C_{12}$-alkyl or branched or straight-chain $C_1$–$C_{12}$-haloalkyl which substitute the ring formed by $R^3$ and $R^4$ and/or the rings fused onto this ring, or the ligand L is a compound of the formula (4) or (5)

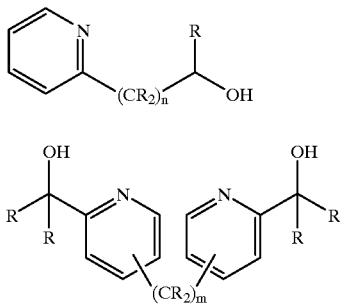

(4)

(5)

where R is hydrogen, $C_1–C_8$-alkyl, $C_1–C_8$-alkoxy, $COOCH_3$, carbonyl oxygen, $C_6–C_{14}$-aryl or $C_3–C_8$-cycloalkyl and n is 1 or 2 and m is from 1 to 6.

The ligand is generally bound in a bidentate fashion to the metal center which can bind up to two such ligands. In the case of the tetradentate ligand (5), only one ligand is bound. The dioxo complexes can be in the form of cis or trans isomers

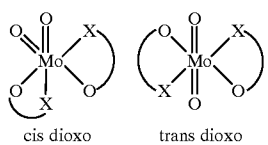

cis dioxo    trans dioxo

Examples of preferred ligands L are the following compounds:

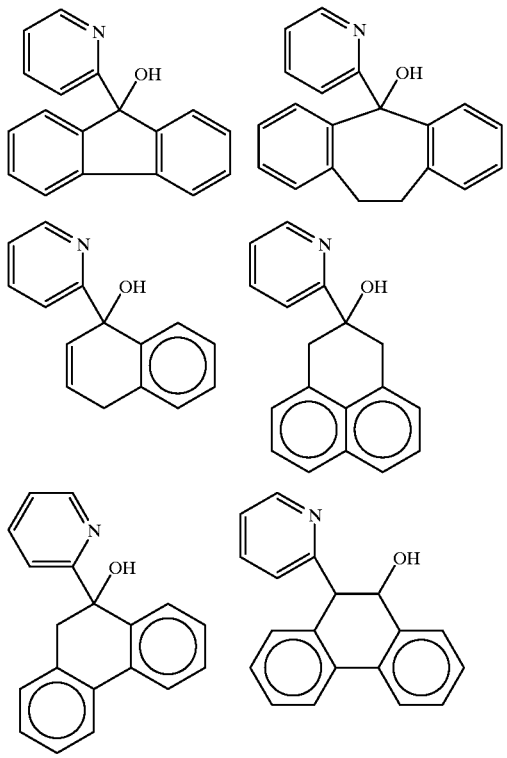

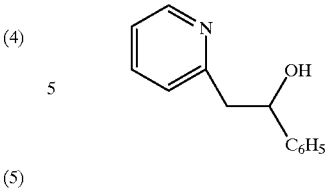

Complexes of the formula (1) are prepared by reacting a suitable precursor with the appropriate ligands in an organic solvent. Suitable precursors are, for example, the commercially available oxo-acetylacetonates such as molybdenyl acetylacetonate $MoO_2(acac)_2$ or oxo-dithiocarbamates, e.g. molybdenyl bis(N,N-diethyldithiocarbamate), the pyridyl and/or acetate complexes of the oxides, the higher oxides, e.g. molybdenum trioxide, or the corresponding acids and their salts.

The precursor is suspended in an organic solvent. Most suitable organic solvents are polar protic solvents such as methanol or ethanol and aprotic solvents such as acetonitrile or methyl tert-butyl ether (MTBE) or halogenated hydrocarbons such as $CH_2Cl_2$, $CHCl_3$ or $CCl_4$.

While stirring, the appropriate ligand is subsequently added, preferably in dissolved form. The amount of ligand used is preferably twice that of the precursor used.

After the reaction is complete, the solvent is removed by filtration and the residue is washed. The filter residue obtained can be used as catalyst in this form or after drying under reduced pressure.

Supported complexes can be prepared by adding a suitable support material during and/or after the synthesis of the complex. Here, the starting complex of the formula (1) is dissolved in an organic solvent or water, the support material is added and the mixture is stirred. The ratio of complex/support material is preferably in the range from 1:1 to 1:1000, in particular in the range from 1:2 to 1:100.

Suitable support materials are inorganic and organic supports. Examples of inorganic supports are aluminum oxides, silicon dioxides, aluminosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride, carbon and silicon carbide.

Suitable organic supports are all polymers possessing donor centers which can undergo interactions with the Mo center, or functionalized polymers which form a chemical bond on reaction with the complexes of the formula 1 or ligands of the formulae (2)–(4). In the latter case, the heterogenized ligand obtained in this way has to be converted into the complex by reaction with a suitable precursor (e.g. $MoO_2(acac)_2$) in an organic solvent. Examples of such supports are polypyridines, polyacrylates and polymers containing $PR_2$, $O=PR_2$ or $NR_2$ (R=H, alkyl, aryl) groups.

The catalysts of the invention allow olefins to be epoxidized selectively using atmospheric oxygen. As oxidizing agent, it is only necessary to use oxygen which can be employed in pure form or as atmospheric oxygen or diluted with an inert gas such as $CO_2$, $N_2$, noble gases or methane.

They are advantageous for the oxidation of aliphatic, branched or unbranched $C_2–C_{30}$-alkenes and $C_5–C_{12}$-cycloalkenes, in particular for the oxidation of linear $C_2–C_{25}$-alkenes and $C_5–C_8$-cycloalkenes, especially for the oxidation of $C_2–C_{12}$-alkenes such as ethene, propene or octene, but epoxides of longer-chain or higher alkenes can also be obtained with the aid of the complexes of the invention. These olefins can also be substituted by further alkyl, alkoxy or aromatic groups and/or by halogens. The oxidation conditions are selected so that appreciable oxidation occurs even without addition of catalyst, but the selectivity to the epoxide is low in this case.

In the epoxidation of octene using the heterogeneous catalysts of the invention, the reaction is generally carried out in a temperature range from 30 to 300° C., preferably in the range from 70 to 130° C. In the case of propene, the temperature is preferably in a range from 100 to 500° C., in particular in the range from 125 to 230° C. The pressure should be in the range from 20 to 200 bar, in particular from 35 to 100 bar.

The liquid-phase oxidation is carried out either in pure olefin or diluted in an oxidation-stable solvent. Suitable solvents are, for example, the following groups: halogenated aromatics such as chlorobenzene, 1-chloro-4-bromobenzene or bromobenzene, halogenated and non-halogenated hydrocarbons such as chloroform, chloropropanol, dichloromethane, 1,2-dichloroethane or trichloroethylene, also alcohols, in particular $C_1$–$C_{12}$-alcohols such as ethanol, methanol or propanol, and also higher alcohols and water.

The invention is illustrated by the following examples.

EXAMPLES

The following ligands were prepared:

Example 1

1,1-Fluorenyl-1-(2-pyridyl)methanol

Example 2

1,1-Suberyl-1-(2-pyridyl)methanol

Ligand Synthesis for Examples 1 and 2

0.12 mol of butyllithium is slowly added dropwise under argon to 300 ml of methyl t-butyl ether which is cooled to −30° C. During this addition, the temperature should not exceed −20° C. Subsequently, 0.13 mol of 2-bromopyridine dissolved in 75 ml of methyl t-butyl ether is slowly added dropwise to the ether solution of BuLi. This results in formation of the red solution characteristic of the organolithium compounds. 0.15 mol of the respective carbonyl compound (fluorenone or suberenone) dissolved in 75 ml of methyl t-butyl ether is then added dropwise to the clear, dark red solution prepared in this way. Here too, the temperature should not exceed −20° C. The solution is stirred for 2 hours at −30° C. and is then slowly warmed to 0° C. and subsequently hydrolyzed carefully with a little distilled water. The solution is then warmed to room temperature and shaken with a little 15% strength hydrochloric acid. The aqueous phase is subsequently neutralized using 15% strength aqueous sodium hydroxide solution and extracted with methyl tert-butyl ether. The ether phase is subsequently evaporated on a rotary evaporator to leave the desired product which is purified by recrystallization (solid product) or distillation (liquid product). The following molybdenum complexes were prepared:

Bis[9-(2'-pyridinyl)fluoren-9-olato]
dioxomolybdenum(VI) (Example 1)

Yield:
Empirical formula: $MoC_{36}H_{24}N_2O_4$
Molar mass: 644.54
MS/EI: 644$^+$ m/e

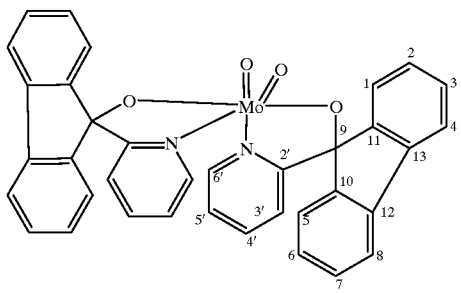

$^1$H-NMR [CDCl$_3$, 20° C., ppm] 9.10 (H$^{6'}$, d $^3$J(H$^{6'}$, H$^{5'}$)=5 Hz, 1H), 7.80 (H$^{3/7}$, dd, $^3$J(H$^{3/7}$, H$^{4/8}$)=8 Hz, $^3$J(H$^{3/7}$, H$^{2/6}$)=8 Hz, 2H), 7.65 (H$^{1/5}$, d, $^3$J(H$^{1/5}$, H$^{2/6}$)=9 Hz, 2H), 7.60 (H$^{4'}$, dd, $^3$J(H$^{1'}$, H$^{3'}$)=8 Hz, $^3$J(H$^{1'}$, H$^{5'}$)=8 Hz, 1H), 7.40 (H$^{5'}$, dd, $^3$J(H$^{5'}$, H$^{6'}$)=6 Hz, $^3$J(H$^{5'}$, H$^{1'}$)=7 Hz, 1H), 7.33 (H$^{2/6}$, m, 2H), 7.33 (H$^{4/8}$, m, 2H), 7.05 (H$^{1/5}$, d, $^3$J(H$^{1/5}$, H$^{2/6}$)=9 Hz, 2H), 6.70 (H$^{3'}$, d, $^3$J(H$^{3'}$, H$^{1'}$)=8 Hz, 1H)

{$^1$H}-$^{13}$C-NMR [CDCl$_3$, 20° C., ppm] 164.86 (C$^2$), 147.82 (C$^{6'}$), 150.85 (C$^{10/11}$), 149.13 (C$^{10/11}$), 141.52 (C$^{12/13'}$), 138.92 (C$^{12/13'}$), 139.04 (C$^4$), 129.66 (C$^{1/5}$), 129.53 (C$^{1/5}$), 129.03 (C$^{3/8}$), 127.52 (C$^{3/8}$), 125.62 (C$^{1/6}$), 124.91 (C$^{1/6}$), 124.91 (C$^{1/6}$), 123.13 (C$^3$), 121.94 (C$^{5'}$), 120.51 (C$^{4/9'}$) 119.63 (C$^{4/9'}$), 120.51 (C$^{1/9'}$), 119.63 (C$^{4/9'}$), 95.56 (C$^9$)

IR[KBr, cm$^{-1}$]: ν(Mo=O)=921(s), 903(s)

Bis[5-(2'-pyridinyl)-10,11-dihydrodibenzo[a,d]
cyclohepten-5-olato]dioxomolybdenum(VI)
(Example 2)

Yield:
Empirical formula: $MoC_{40}H_{32}N_2O_4$
Molar mass: 700.65
EA calc.: H, 4.60; C, 68.57; N, 4.00.
EA found: H, 5.04; C, 67.63; N, 3.50.

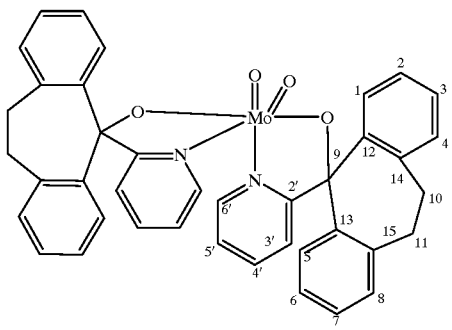

$^1$H-NMR [CDCl$_3$, 20° C., ppm] 7.68 (H$^{1/6}$, d,$^3$J(H$^{1/6}$, H$^{2/7}$)=9 Hz, 2H), 7.40 (H$^{6'}$, d, $^3$J(H$^{6'}$, H$^{5'}$)=5 Hz, 1H), 7.53 (H$^{4'}$, dd, $^3$J(H$^{4'}$, H$^{3'}$)=8 Hz, $^3$J(H$^{4'}$, H$^{5'}$)=8 Hz, 1H), 7.21 (H$^{3/8}$, dd, $^3$J(H$^{3/8}$, H$^{2/7}$)=7 Hz, $^3$J(H$^{3/8}$, H$^{4/9'}$)=7 Hz, 2H) 6.98 (H$^{5'}$, dd, $^3$J(H$^{5'}$, H$^{6'}$)=6 Hz, $^3$J(H$^{5'}$, H$^{4'}$)=7 Hz, 1H), 6.91 (H$^{2/7}$, dd, $^3$J(H$^{2/7}$, H$^{3/8}$)=8 Hz, $^3$J(H$^{2/7}$, H$^{1/6}$)=8 Hz, 2H), 6.90 (H$^{3'}$, d, $^3$J(H$^{3'}$, H$^{4'}$)=8 Hz, 1H), 6.50 (H$^{4/9}$, d, $^3$J(H$^{4/9}$, H$^{3/8}$)=8 Hz, 1H), 6.38 (H$^{4/9}$, d, $^3$J(H$^{4/9}$, H$^{3/8}$)=8 Hz, 1H), 4.15 (H$^{11/12}$, m 1H), 3.80 (H$^{11/12}$, m 1H), 3.15 (H$^{11/12}$, m 2H).

{$^1$H}-$^{13}$C-NMR [CDCl$_3$, 20° C., ppm] 167.21 (C$^2$), 147.64 (C$^{6'}$), 142.13 (C$^{15/16}$), 143.62 (C$^{15/16}$), 141.45

($C^{12/13'}$), 137.98 ($C^{12/13''}$), 136.51 ($C^{4'}$), 132.05 ($C^{2/7}$), 130.81 ($C^{2/7}$), 130.64 ($C^{3/8}$), 129.85 ($C^{3/8}$), 128.24 ($C^{1/6}$), 127.87 ($C^{1/6}$), 126.25 ($C^{4/9'}$), 126.25 ($C^{4/9'}$), 124.95 ($C^{3'}$), 124.91 ($C^{4/9'}$), 122.83 ($C^{5'}$), 96.64 ($C^5$), 35.33 ($C^{10/11}$), 34.78 ($C^{10/11}$).

IR[KBr, cm$^{-1}$]: ν(Mo=O)=915(s), 895(s)

Oxidation of 1-octene 2.0 ml (12.6 mmol) of 1-octene and 80 μmol of the respective catalyst are placed in a 10 ml reactor (septum, reflux condenser-gas burette). The apparatus is flushed with O$^2$, filled with a pure O$_2$ atmosphere (1 bar) and subsequently heated to 100° C. After an O$_2$ uptake of 10 ml, the reaction is stopped by cooling, 1 ml of the reaction solution is admixed with exactly 50 μl of heptane (internal GC standard) and the selectivity to 1,2-epoxyoctane is determined by gas chromatography.

Employing the above procedure, 1-octene was epoxidized using molybdenum complexes of the prior art (Comparative Examples 1–3) and the molybdenum complexes of the invention (Examples 1–2). The following results were obtained:

80 μmol of the respective catalyst are placed in a cleaned 200 ml autoclave and dissolved using 20 ml of chlorobenzene. After addition of the stirring device (magnetic stirrer bar), the autoclave is closed and cooled to −15° C. by means of an isopropanol/dry ice mixture. About 27 g of propene are subsequently condensed in. After the apparatus has been tested for freedom from leaks, the starting material mixture is heated to 150° C. while stirring. When it has reached 150° C., 10 bar of synthetic air are injected. The reaction is then carried out for 4 minutes at 150° C. and the mixture is subsequently cooled. The reaction mixture which has been cooled to room temperature is then carefully vented via the gas sampling point. At the commencement of venting, the sample for gas analysis is taken. After the autoclave has been completely depressurized, the sample of the liquid phase for GC analysis is taken.

| Examples | Catalyst | Selectivity to 1,2-epoxyoctane | Selectivity to propylene oxide |
|---|---|---|---|
| Comparative Example 1 | MoO$_2$(acac)$_2$ | 7% | not determined |
| Comparative Example 2 | MoO$_2$("Bu")$_2$ | 46% | 72% |
| Comparative Example 3 | MoO$_2$("phenyl")$_2$ | 45% | 63% |
| Example 1 | MoO$_2$("fluorenyl")$_2$ | 50% | 62% |
| Example 2 | MoO$_2$("suberyl")$_2$ | 62% | 56% |

"Bu" = 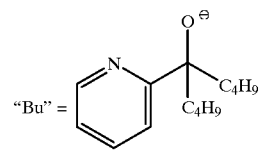

"phenyl" = 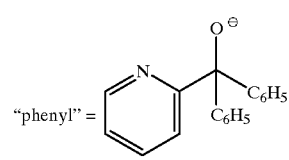

What is claimed is:

1. A catalyst for the selective oxidation of olefins in the presence of air or oxygen, comprising a compound of the formula (1)

$$Mo_xO_y(L)_z \quad (1)$$

where x is 1, 2 or 3, y is an integer from 0 to 2x+1, z is an integer from 1 to 2x, where x is 1, 2 or 3, y is an integer from 0 to 2x+1, z is 1, wherein the ligand L is a compound of the formula (2) or (3)

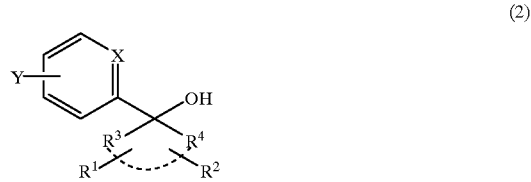

(2)

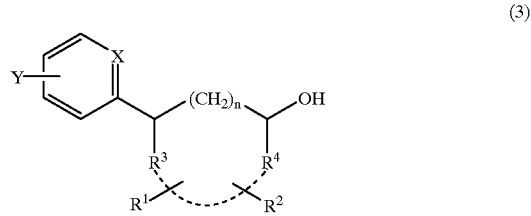

(3)

where n is 0 or 1,

X is a nitrogen, oxygen or sulfur atom,

Y is hydrogen, C$_{1-C8}$-alkyl, C$_1$–C$_8$-alkoxy, F, Cl, Br, I, COOCH$_3$, C$_6$–C$_{14}$-aryl or C$_3$–C$_8$-cycloalkyl, R$^3$ and R$^4$ form a ring containing from 4 to 8 carbon atoms onto which one or two aromatic rings may be fused, R$^1$ and R$^2$ are hydrogen, branched or straight-chain C$_1$–C$_{12}$-alkyl or branched or straight-chain C$_1$–C$_{12}$-haloalkyl which substitute the ring formed by R$^3$ and R$^4$ and/or the rings fused onto this ring, or the ligand L is a compound of the formula (4) or (5)

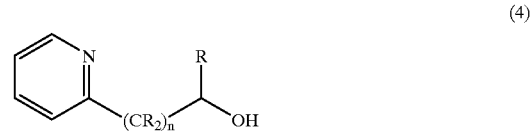

(4)

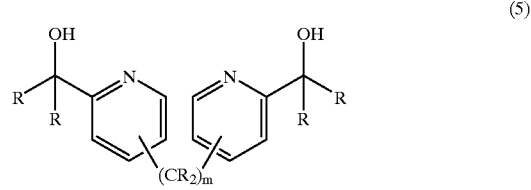

(5)

where R is hydrogen, C$_1$–C$_8$-alkyl, C$_1$–C$_8$-alkoxy, COOCH$_3$, carbonyl oxygen, C$_6$–C$_{14}$-aryl or C$_3$–C$_8$-cycloalkyl and n is 1 or 2 and m is from 1 to 6.

2. A catalyst for or the selective oxidation of olefins in the presence of air or oxygen, comprising a compound of the formula (1)

$$Mo_xO_y(L)_z \quad (1)$$

wherein the ligand L is one of the following compounds:

(a) 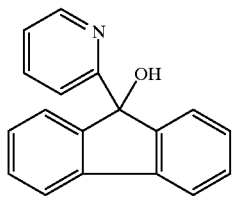

(b) 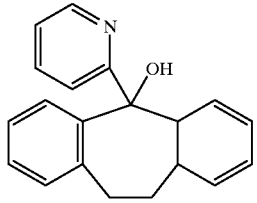

(c) 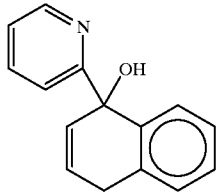

(d) 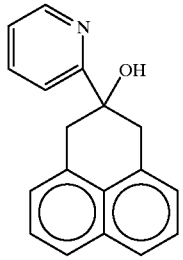

(e) 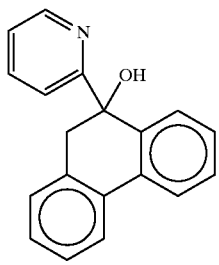

(f) 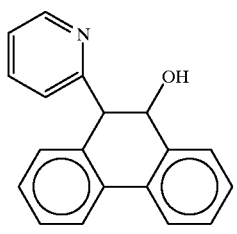

(g) 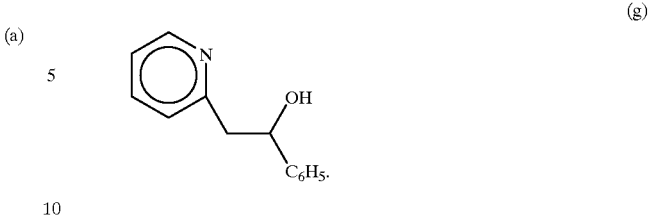

3. A catalyst as claimed in claim 2, wherein said catalyst thereof is applied to a support material, wherein the ratio of complex/support material is in the range from 1:1 to 1:1000.

4. A catalyst as claimed in claim 3, wherein the support material is selected from the group consisting of aluminum oxides, silicon dioxides, aluminosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride, silicon carbide, polypyridines, polyacrylates and polymers containing $PR_2$, $O=PR_2$ or $NR_2$, where R=H, alkyl or aryl, groups.

5. The catalyst as claimed in claim 2, wherein said catalyst is applied to a support material, wherein the ratio of complex/support material is in the range from 1:2 to 1:100.

6. The catalyst as claimed in claim 2, wherein $y \geq 1$ and $2y+z$ is 5 or 6.

7. A catalyst for the selective oxidation of olefins in the presence of air or oxygen, comprising a compound of the formula (1)

$$Mo_xO_y(L)_z \qquad (1)$$

where
x is 2 or 3,
y is an integer from 0 to 2x+1,
z is an integer from 1 to 2x,
wherein the ligand L is a compound of the formula (2) or (3)

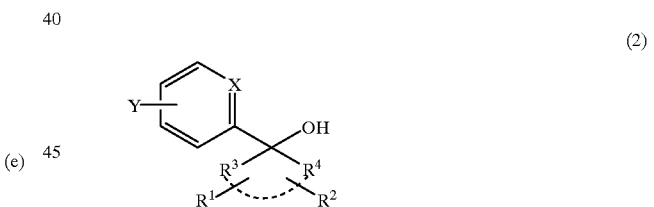

where
n is 0 or 1,
X is a nitrogen, oxygen or sulfur atom,
Y is hydrogen, $C_1$–$C_8$-alkyl, $C_1$–$C_8$-alkoxy, F, Cl, Br, I, $COOCH_3$, $C_6$–$C_{14}$-aryl or $C_3$–$C_8$-cycloalkyl,
$R^3$ and $R^4$ form a ring containing from 4 to 8 carbon atoms onto which one or two aromatic rings may be fused, $R^1$ and $R^2$ are hydrogen, branched or straight-chain $C_1$–$C_{12}$-alkyl or branched or straight-chain $C_1$–$C_{12}$-haloalkyl which substitute the ring formed by $R^3$ and $R^4$ and/or the rings fused onto this ring, or the ligand L is a compound of the formula (4) or (5)

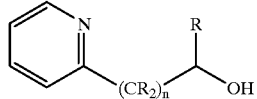
(4)

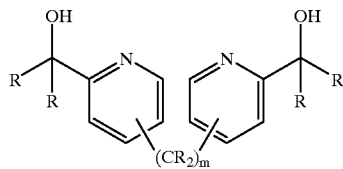
(5)

where R is hydrogen, $C_1$–$C_8$-alkyl, $C_1$–$C_8$-alkoxy, COOCH$_3$, carbonyl oxygen, $C_6$–$C_{14}$-aryl or $C_3$–$C_8$-cycloalkyl and n is 1 or 2 and m is from 1 to 6.

* * * * *

UNITED STATES PATENT AND TRADEMARK OFFICE
CERTIFICATE OF CORRECTION

PATENT NO. : 6,248,913 B1
DATED : June 19, 2001
INVENTOR(S) : Lobmaier et al.

Page 1 of 1

It is certified that error appears in the above-identified patent and that said Letters Patent is hereby corrected as shown below:

Column 8,
Line 29, "$C_1-C_8$" should read -- $C_1-C_8$ --.
Line 57, "for or the" should read -- for the --.

Signed and Sealed this

Eleventh Day of December, 2001

Attest:

*Nicholas P. Godici*

NICHOLAS P. GODICI
*Attesting Officer*   *Acting Director of the United States Patent and Trademark Office*